United States Patent [19]

Bicer

[11] Patent Number: 4,494,253
[45] Date of Patent: Jan. 22, 1985

[54] CARDIOVASCULAR VALVE PROSTHESIS

[76] Inventor: Demetrio Bicer, Warnes St. No. 2682, Buenos Aires, Argentina

[21] Appl. No.: 567,806

[22] Filed: Jan. 3, 1984

[30] Foreign Application Priority Data

Oct. 28, 1980 [AR] Argentina ............................. 283040

[63] Related U.S. Application Data Continuation-in-part of Ser. No. 312,906, Oct. 19, 1981, abandoned

[51] Int. Cl.³ ............................................... A61F 1/22
[52] U.S. Cl. .......................................................... 3/1.5
[58] Field of Search ......................................... 3/1.5, 1

[56] References Cited

U.S. PATENT DOCUMENTS

| 3,476,143 | 11/1969 | Kaster | 3/1.5 X |
| 3,824,629 | 7/1974 | Shiley | 3/1.5 |
| 3,835,475 | 9/1974 | Child | 3/1.5 |
| 3,859,668 | 1/1975 | Anderson | 3/1.5 |
| 3,997,923 | 12/1976 | Possis | 3/1.5 |
| 4,057,857 | 11/1977 | Fettel | 3/1.5 |
| 4,276,132 | 6/1981 | Fettel et al. | 3/1.5 X |

Primary Examiner—Ronald L. Frinks
Attorney, Agent, or Firm—Allegretti, Newitt, Witcoff & McAndrews, Ltd.

[57] ABSTRACT

A cardiovascular valvular prosthesis and a method for its manufacture are disclosed. The prosthesis consists of a support having a perimetral groove thereon and an occluding disc which is assembled on the support. The occluding disc is freely rotatable. A textile ring is adapted in the perimetral groove and consists of a tubular fabric.

8 Claims, 6 Drawing Figures

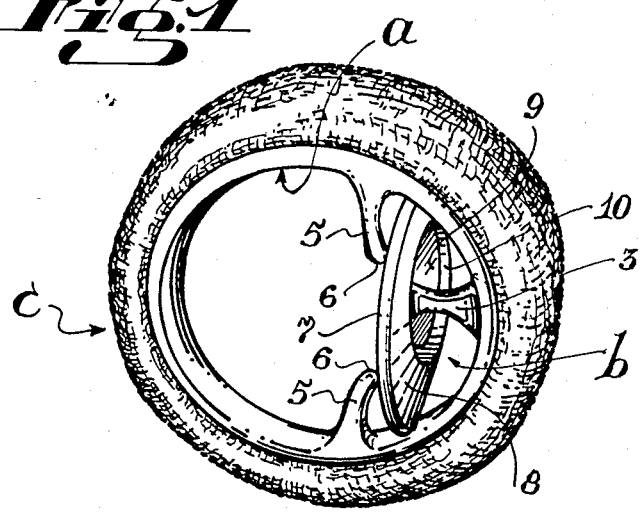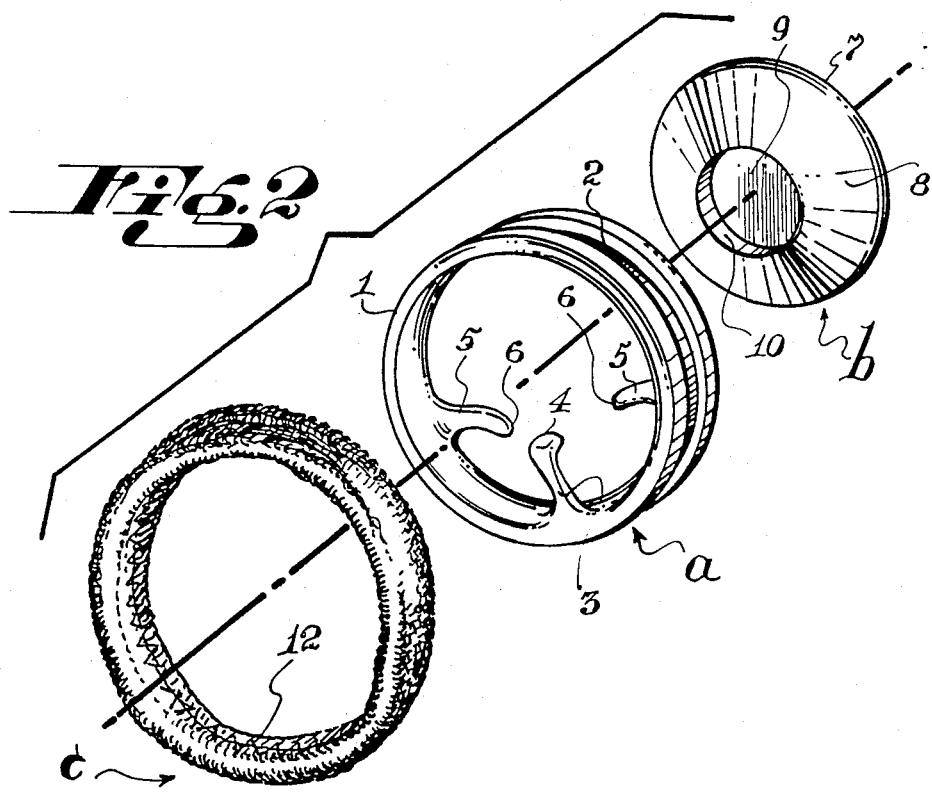

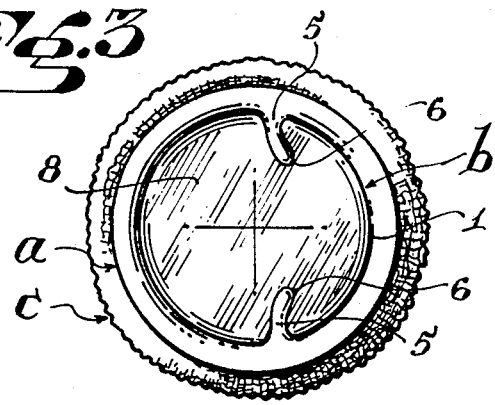
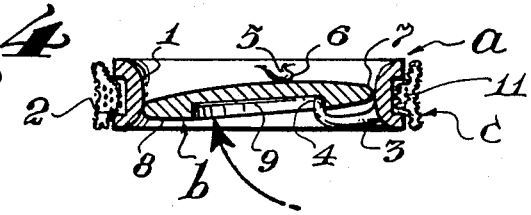
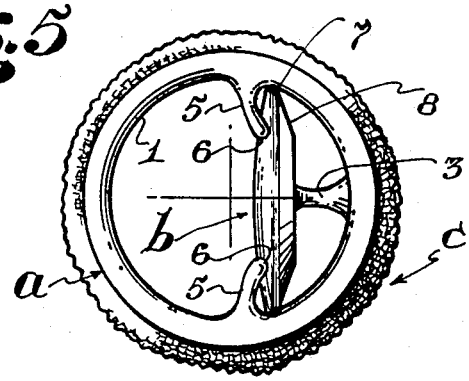
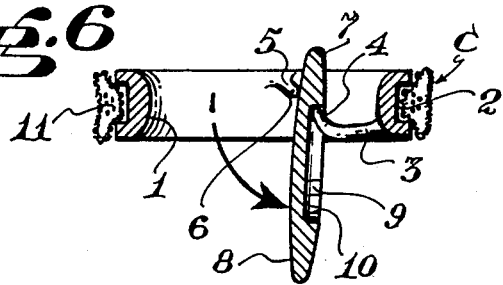

CARDIOVASCULAR VALVE PROSTHESIS

This is a continuation of application Ser. No. 312,906, filed Oct. 19, 1981, now abandoned.

BACKGROUND AND SUMMARY OF THE INVENTION

The present invention relates to a cardiovascular valvular prosthesis and a process for manufacturing a cardiovascular prosthesis. The prosthesis advantageously solves some of the problems encountered in the cardiac valves presently known.

Persistent problems of reliability have necessitated the adoption of regulations, in many countries, for the use of said prostheses. The regulations typically contain requirements which attempt to eliminate possible disadvantages to the user and the danger arising from eventual complications subsequent to the implantation of prostheses.

Although at present different types and models of cardiac valves exist in the world, some of them, once they have been implanted in the patient, develop anomalies and problems that in certain cases may cause the death of the patient. It was evidenced in one particular case, published in the May, 1980 "Briefcase", edited by Regulatory Associates Inc., in which the manufacturer of the prosthesis, Shiley Lab. of Irvine, Calif., U.S.A., was notified by Dr. Viking Bjork, an outstanding cardio-surgeon of the Karolinska Institute of Stockholm, Sweden, of a prosthesis, 18 months after being implanted, in which the valve support had sustained a fracture.

With reference to this matter, the Executive Secretary of the Classification Panel of Cardiovascular Design in the United States has stated that the above mentioned incident is only one of many other incidents and that the majority of the valves that have failed have failed due to durability problems. Problems such as defective design and a lack of attention in the engineering details have contributed to many valve failures.

The valve, discussed above, which failed had been patented in the United States in October 1972. The valve has an occluding disc held between spaced elements which form, in a support ring, crossbars with folded portions. The longest of the crossbars have a middle portion approximately coincident with the diameter of the occluding disc, both being of a substantially "U" shape. The angle of maximum opening of the disc is 62 degrees. The disc is constructed of an acetal resin formed by the polymerization of formaldehyde having a high crystallization structure.

In the Sorin valve, the opening angle of the occluding disc is on the order of 61 to 68 degrees. The supports of the valve have a similar shape as that of the valve known as the Shiley valve discussed above.

The durability problems of the valves can be attributed to mechanical characteristics in the manufacture of the supports which are generally used in the shape in which they are cast. In other cases, the supports must be welded to the "U" shaped transversal means which support the disc.

In any of the above mentioned cases, it is almost impossible to assure that the supports will not have weak areas, either because the casting does not offer the same guarantees as the machined material or because the welded areas crack due to the many movements to which they are subjected.

It must be taken into consideration that a cardiac valve must endure an average of 45 million cycles per year when this figure is multiplied by the minimum life expectation.

Contact between valve surfaces should be limited in every way possible, in order to avoid damage to the blood through compression that could lead to irreparable clinical consequences such as microembolisms and the formation of clots through adherence. It is also desirable to obtain the greatest free circulation area possible and to offer the least resistance to the passage of the blood flow. In the case of the above mentioned valves, the support means of the occluding disc, the opening angle of which does not reach to 70 degrees, are interpolated in the flow passage which they divide, thereby creating hemodynamic resistance and the possibility of creating turbulence.

Another matter to be considered is the textile ring that is fixed to the valve. The ring is usually formed by sewing the ends to give the adequate form. This requires a transversal suture, the joining filaments of which can loosen due to failure of the ring or fatigue during its use.

In the prosthesis generally used presently, the occluding disc is not radiopaque and, thus, does not allow its visualization for control by means of X-rays during the patient's clinical followup. This prevents the effecting of a correct cardiac catheterism.

All the above mentioned disadvantages have been solved by the valvular prosthesis of the present invention, the concept of which is completely novel and the results of which have been optimum. The evaluation of prosthesis of the present invention has been effected by the Biomedical Engineering and the Mechanical Engineering Departments of Tulane University, in New Orleans, La. The evaluation was carried out in an environment which simulated the geometrical characteristics as well as the dynamics of the human left ventricle using a fluid similar to blood. The valve prototypes submitted for evaluation that corresponded to the invention were in the mitral position and in the aortic position in a chamber especially designed for the type of study conducted.

It has been found that, due to the quality of the material used for the support of the occluding disc as well as the particular shape of the disc, and as a result of its manufacturing process, the unit presents unusual physical, mechanical and chemical characteristics and superior performance. It has also been found that the support is practically inert to solutions, acids, or alkalis at room temperature.

The support is not manufactured by casting or by welding the supports of the occluding disc, as is done in the prior art. In the manufacturing process of the present invention, the morphologic structure of the alloy used is maintained without altering the position of the crystals and thus keeps the physical as well as the chemical characteristics of the support constant.

Furthermore, due to the special shape and position of the support means of the occluding disc, which does not have radial lateral arms, bulkiness at the ends, or bondings, a larger free passage area is offered without obstacles in the central portion, thereby obtaining a flow with a minimum resistance to the passage of fluid and practically eliminating the possibility of causing turbulence.

Another advantage of the present invention is that the opening of the occluding disc varies between 85 and 90 degrees, thereby providing low profile and minimum hemodynamic resistance.

Yet another advantage of the present invention lies in the shape of the occluding disc which, when in an open position, fixes a laminar flow against the faces of the disc. When the disc is in closed tangential contact, it allows a small peripheric insufficiency between the disc and the support which allows the washing of the internal surface of the support with the same blood through the action of the blood flow and the non-static accumulating of blood during the systole period when the valve is closed.

Still another advantage of the present invention is the fact that the occluding disc is manufactured with carbon substrate (graphite) with a mixture on the order of 5% of tungsten which is perfectly visible in X-rays and allows the clinical follow-up control of the patient. The material of the disc is biocompatible with blood and is thrombo-resistant.

Another advantage of the present invention is established by the construction and fixing of the textile ring or fixing hoop of the prosthesis, which does not present transversal sutures or seams for joining its ends. It is effected in one piece and thus offers higher resistance and prevents the risk of breakage by loosening or failure of the threads or fatigue during use, with the consequent risk of loosening the valve. It must be taken into account that the prosthesis, in its position, performs a slight movement on the commissural stitches as a consequence of the difference of the pressure between the systole and the diastole.

Another very important advantage of the present invention is provided by the fact that the occluding disc, due to its special assembly, can freely rotate within its support. During the operation of the prosthesis of the present invention, this free rotation allows an alternate contact of the surfaces of the disc with the support arms, thereby avoiding wear of the disc on one only surface, thereby evenly distributing the work and wear by friction or fatigue to which the disc is submitted.

In the present invention, the fixing textile ring may be freely rotated over the housing groove in the support, thereby permitting the surgeon to carry out an operation to correct in situ any variation in the position of the valve that may be considered advisable during the implantation operation and also once the valve is fixed by means of sutures. This eliminates the need to withdraw the sutures to reset the valve when the position of the valve must be corrected, thereby eliminating the consequent complications of loss of time and the eventual surgical risk for the patient.

The valve of the present invention offers excellent clinical expectations, reduces risks and the possibility of embolism and its consequences, hemodynamic turbulences and their clinical complications to the extent that, even by using non-thrombogenic materials acceptable in the manufacture of the valve, the use of anticoagulant drugs can be avoided in the post-operation treatment of the patient. At present the use of such drugs constitutes a constant preoccupation for the patient as the drugs must be injected periodically and the use extends during the patient's life time with the consequent discomfort and trauma.

Other characteristics and advantages of the present invention may be appreciated from the following description of the preferred embodiment of the present invention and the attached drawing which illustrates the cardiovascular valvular prosthesis in its preferred embodiment.

BRIEF DESCRIPTION OF THE DRAWING

FIG. 1 is a perspective view of the cardiovascular valvular prosthesis of the present invention illustrating the prosthesis in its maximum opening position, that allows to appreciate its characteristics as a whole.

FIG. 2 is a perspective view of the disassemblied valvular prosthesis of the present invention, in which the basic component pieces may be observed.

FIG. 3 is an elevated front view of the prosthesis of the present invention, in the closed position, shown from the fluid inlet side through the prosthesis.

FIG. 4 is a transverse sectional view of the prosthesis of the present invention shown in the closed position of FIG. 3, in which the arrow points to the angular displacement of the occluding disc toward the closed position.

FIG. 5 is a front view, similar to that of FIG. 3, which illustrates the opening position of the occluding disc of the present invention.

FIG. 6 is a sectional view, similar to that of FIG. 4, which illustrates the opening position of FIG. 5, the arrow indicating the angular displacement of the occluding disc toward the opening position.

DESCRIPTION OF THE PREFERRED EMBODIMENT

In the different figures, the same reference numbers indicate equal or corresponding parts. A unit composed of several elements has been designated with a letter.

With reference to FIGS. 1-6, the cardiovascular valvular prosthesis of the present invention comprises three pieces properly connected to each other: The first is a support a which comprises a substantially rigid body manufactured with a special biocompatible alloy based on a high grade cobalt. The second piece is an occluding disc b, assembled with angular displacement possibilities on said support a, manufactured from isotropic pyrolitic carbon with tungsten radiopaque incrustations. Disc b is also biocompatible and thromboresistant and has great resistance to degrading by use and fatigue within the prosthesis, the particular outline of which in the opening position, provides the maintenance of a laminar flow with a minimum hemodynamic resistance. The third piece is a textile hoop or ring c, manufactured in one piece, that is permanently affixed to support a and by means of sutures constitutes the fixing means of the assembly.

Support a is constructed of an integrally machined piece consisting of an annular portion 1 in the external face on which a circumferencial groove 2 is defined adapted to cooperate with the textile ring c.

A support arm 3 projects from an edge of annular portion 1 towards the inner portion of annular portion 1 and in a radial direction. Support arm 3 ends in a terminal 4, which at a distance from the center of annular portion 1, projects toward the inner portion, that is, toward the face opposite to that of the position of arm 3, as may observed in FIGS. 2, 4 and 6.

On both sides of support arm 3, equidistant from arm 3 and projecting from the opposite edge of the annular portion 1, a set of support arms or fingers 5 project according to a virtual cord displaced with respect to the diameter of the annular portion 1. The fingers 5 are shaped in such a way that their terminals 6 define the support means of the occluding disc b placed between the terminals 6 and the terminal 4 of the intermediate arm 3.

Thus, support arm 3 and fingers 5 are separated from each other and in different planes of the annular portion 1, as may be observed in FIGS. 4 and 6. The occluding disc b is adapted in a floating position with three tangential contact points with those corresponding to the terminals 4 and 6 of support arm 3 and fingers 5 and with the possibility, aside from its angular displacement in the manner shown by the arrows in FIGS. 4 and 6, of rotation as mentioned above.

Due to the particular shape of the support arm 3 and fingers 5 and the displaced position of fingers 5 with reference to the diameter of the annular body 1 of support a, the occluding disc b has a substantially free area in its opening position which determines a flow (FIGS. 1 and 5) with a minimum hemodynamic resistance of said occluding disc b.

The profile of disc b shows a rounded perimetral edge 7, with divergent sides 8 that correspond to the convexity of the faces of disc b, the side placed facing the intermediate support arm 3 having a central depression 9, the internal edge of which, in the closed position, defines a step 10 against which terminal 4 of said arm 3 abuts. Terminal 4 defines a pin, as may be observed in FIGS. 4 and 6.

The external perimetral groove 2 of support a cooperates with the textile ring c that consists of a single piece of "Dacron" fabric, made in a tubular form, held by multifilament threads of the same material. In its manufacture, groove 2 forms a kind of nucleus of said ring c and fastens ring c to support a.

Many of the novel characteristics of the prosthesis of the present invention, particularly that regarding support a and the textile ring c that holds the unit in position by means of sutures.

Support a is manufactured in a single piece without casting or welding and without any deformation of the alloy used due to forging, temperature or any other system that can negatively modify the properties of the metal.

For this purpose, the alloy bar is machined and cast by means of a Laser ray so as to shape within the internal portion of the annular body 1 thus obtained, a middle arm 3 on one side and the fingers 5 on the other side of body 1. The casting process is effected on both sides to obtain this result. Subsequently, the piece is shaped by means of electroerosion, thus obtaining the final shape of the fingers 5. The piece is finished with a final polish and manual adjustment.

The piece is only superficially affected by temperature dissipation. This is eliminated by means of the finishing process, without affecting the alloy of the piece obtained.

The occluding disc b is formed from a carbon substrate, graphite, known as isotropic pyrolitic carbon, that has a coating that consists of the special bath of thermal deposit carbon which offers the best characteristics for this type of valve due to its biocompatibility with blood, particularly its thromboresistance together with high resistance to degradation due to use and fatigue in the prosthesis.

Disc b is assembled on support a in a floating adaptation between support arm 3 and fingers 5, with freedom to rotate. This allows alternative contacting of the opposed surfaces of disc b with terminals 4 and 6 of arms 3 and fingers 5, which eliminates the possibility of wear and/or fatigue in fixed points of disc b.

The suture textile ring c is made by cutting an adequate measure of a "Dacron" fabric tube, obtained in tubular form from adequate circular machines, which is placed on the external portion of support a as a cover over the perimetral groove 2 of support a.

Subsequently, five turns 11 with a multifilament thread, also of "Dacron", made on the fabric around groove 2, conveniently knotting the thread at intervals of each turn. In this way the textile material, by means of the thread and the knots, is held onto support a. Then the perimetral edges of the tubular fabric are joined together by means of a longitudinal seam 12, perimetral to the support.

The fabric is then dampened and withdrawn from support a, turning the ring c inside out so that the above mentioned longitudinal seam 12 is turned to the inside. Ring c is kept damp and is again placed over groove 2 of support a by means of a dilator and finally, the unit is placed in an oven at an adequate temperature in order to fix the fabric in the compression. Thus, on producing the physical phenomenon of shrinkage when it is dried, the textile ring c is fixed on support a with the assisting retention supplied by the perimetral edges that delimit groove 2 of the housing of support a.

The assembly of the occluding disc b and that of the suture textile ring c on support a may be effected indistinctly first one and then the other, without varying the final finishing result of the valve.

In the assembly, support a with the occluding disc b in position are rotatable with respect to the textile ring c. This means that there is a possibility that textile ring c may slip, which allows the surgeon to place the valve in its desired position once the textile ring c is sutured in its place.

Once the valve has been implanted, the subsequent cellular coverage that pentrates the fabric completes the desired biologic effect for fixing.

It is doubtless that in putting the present invention into practice some modifications may be introduced as regards certain details, without this involving a departure from the basic principles of the present invention which are clearly specified in the following claims.

I claim:

1. A cardiovascular valvular prosthesis comprising in combination an annular support having an outer circumferential groove carrying a textile ring the interior circumference of said annular support having an intermediate support arm and a pair of fingers integrally formed with said annular support and extending into the inner space thereof said support arm lying on a radius of said annular support and terminating short of the center thereof in a rounded contact surface said fingers lying on a chord of said annular support between a diameter of the support and the terminus of said support arm, said chord being normal to said radius and in a plane parallel to the plane of said annular support and spaced from a similar parallel plane through said support arm, the ends of said fingers being curved toward the terminus of said support arm and forming rounded contact surfaces an occluding disc mounted for free axial rotation and partial angular displacement within said annular support solely by point contact with the contact surface of said support arm on one side and the contact surfaces of said fingers on the other side, the area of said contacts when the valve is closed being substantially the same as the area of said contacts when the valve is open the distance between the contact surface of said fingers and the contact surface of said support arm being such as to permit the disc to be disposed, when in open position, at a maximum angle of between 85° and 90° with respect to its closed position, thereby providing passages through said support and around the disc which facilitate free fluid flow with minimum turbulence.

2. The prosthesis of claim 1 wherein said fingers are tapered toward their ends and the diameter of said occluding disc is slightly smaller than the inner diameter of said annular support, the resulting slight play between the periphery of the disc and the inner periphery of the annular support causing a washing flow when said disc is in the closed position.

3. The prosthesis of claim 1 wherein said textile ring is in the form of a tubular strip anchored to the bottom of said annular groove by a plurality of turns of circumferential anchoring threads and the borders of which are joined by a peripheral suture.

4. The prosthesis of claim 1 in which said annular support, said fingers and said support arm are machined from a single piece of metal, and said support arm is of smaller cross-section between its ends than at its ends.

5. The cardiovascular valvular prosthesis of claim 1 wherein said disc is tapered toward its circumferential edge, has a central depression in one face contacted by said support arm and an opposed convex face contacted by said fingers.

6. The cardiovascular valvular prosthesis of claim 5 wherein said depression defines a circumferential step against which the contact surface of said support arm bears.

7. A method for the manufacture of a cardiovascular valvular prosthesis, which comprises:
   (a) machining an alloy bar containing cobalt, thereby forming a machined piece, said piece having an external groove thereon;
   (b) casting said machined piece through the utilization of a laser, thereby forming a radially oriented support arm and a pair of projections extending from said arm, said arm having terminals;
   (c) shaping said piece to obtain the final shape of said arm and said projections and to adjust the prosthesis;
   (d) manufacturing an occluding disc, said disc having a support piece having an external diameter, a substantially convex face and an opposite face disposed opposite to said convex face, said opposite face having a circular central recess, said disc being floatingly adaptable between said terminals of said support arm and said projections arranged symmetrically with respect to said arm;
   (e) cutting a length of tubular fabric, said fabric having a diameter substantially equal to said external diameter of said support piece of said disc, said fabric having perimetral edges;
   (f) covering said external groove with said tubular fabric;
   (g) winding a thread on said external groove and adequately knotting said thread at intervals of each turn;
   (h) joining said perimetral edges of said fabric through the utilization of a longitudinal seam;
   (i) dampening said fabric;
   (j) withdrawing said fabric from said support piece, thereby forming a textile ring, said ring having an inner portion;
   (k) turning said textile ring inside out thereby leaving said longitudinal seam along said inner portion of said textile ring; pl (l) placing said ring, said ring being damp, in position on said groove; and,
   (m) drying the prosthesis thus formed to recover said ring by shrinkage of said fabric, said ring having an internal wound thread.

8. The method for the manufacture of a cardiovascular valvular prosthesis of claim 7 wherein said occluding disc is formed from isotropic pyrolytic carbon, said disc having carbon thermally deposited thereon from a carbon bath, thereby forming a coating on said disc.

* * * * *